United States Patent [19]

Millar et al.

[11] 4,449,980

[45] May 22, 1984

[54] METHODS OF MAKING INTRA-VAGINAL DEVICES AND/OR INTRA-VAGINAL DEVICES

[75] Inventors: Thomas D. Millar; David M. Miller, both of Hamilton, New Zealand

[73] Assignee: AHI Operations Limited, Manukau City, New Zealand

[21] Appl. No.: 269,974

[22] Filed: Jun. 3, 1981

[30] Foreign Application Priority Data

Jun. 9, 1980 [NZ] New Zealand .......................... 193976

[51] Int. Cl.³ ............................................... A61M 7/00
[52] U.S. Cl. ..................................... 604/890; 128/130
[58] Field of Search .......................... 128/130, 127–132; 424/19–22; 604/890–897

[56] References Cited

U.S. PATENT DOCUMENTS

| | | | |
|---|---|---|---|
| 3,703,896 | 11/1972 | Nuwayser | 128/130 |
| 3,710,795 | 1/1973 | Higuchi et al. | 128/130 |
| 4,012,497 | 3/1977 | Schopflin | 128/130 |
| 4,094,313 | 6/1978 | Komamura et al. | 128/130 |
| 4,202,329 | 5/1980 | Kortum | 128/130 |

*Primary Examiner*—Benjamin R. Padgett
*Assistant Examiner*—T. J. Wallen
*Attorney, Agent, or Firm*—Holman & Stern

[57] ABSTRACT

An intra-vaginal device for supplying minerals, hormones or medicoments to an animal is formed as an injection moulded polymeric body having a skin in which adjacent at least part of the surface thereof at least one active ingredient is incorporated. The body is preferably separately moulded before the skin is applied and the skin is preferably of a two part silicone rubber or a polymer such as ethylene vinyl acetate or a polymer substance and the active ingredient is selected from one or more of progesterone oestrogen testosterone, mineral trace elements such as selenium cobalt copper and boron and anthelmintics.

15 Claims, 4 Drawing Figures

METHODS OF MAKING INTRA-VAGINAL DEVICES AND/OR INTRA-VAGINAL DEVICES

This invention relates to methods of making intra-vaginal devices and/or intra-vaginal devices.

SUMMARY OF THE INVENTION

It is an object of the present invention to provide methods of making intra-vaginal devices and/or intra-vaginal devices which will at least provide the public with a useful choice.

Accordingly in one aspect the invention consists in a method of manufacturing an intra-vaginal device, said method comprising the steps of forming a body and incorporating a skin in said skin adjacent at least part of the surface thereof at least one active ingredient.

In a further aspect the invention consists in intra-vaginal device comprising a body including a skin over at least part of the outer surface, at least part of said body being an injection moulding and said skin having in at least parts thereof adjacent the exposed surface thereof at least one active ingredient.

BACKGROUND OF THE INVENTION

In many situations the physiology or pharmacology of an animal process is well enough understood that it can be manipulated by active ingredients such as hormones, drugs and minerals, but the exploitation is limited by the lack of practical methods of administering the active ingredients.

For example, oestrus synchronisation by progestogens in sheep and cattle has been known for more than 30 years but neither injection or feeding sheep or cows is a practical procedure especially under pastoral conditions.

As well as the practical difficulties involved in the administration of drugs, the question of residues is becoming increasingly important. In many cases it is unacceptable to the Authorities, such as the Animal Remedies Board to have animals injected with drugs. The question of possible residues of substances after injection is an increasing concern to such Authorities. This concern may be amplified by restrictions imposed overseas by the U.S. Federal Drug Administration and its E.E.C. equivalents. An outstanding example of this is the banning of stilboestrol in the U.S. despite the fact that carcass residues have never been demonstrated.

The present invention in the preferred form proposes the incorporation of an active ingredient in the skin of a two part device having a body and the skin and for example the active ingredient may be progesterone or an oestrogen or a mineral trace element such as selenium cobalt and copper and boron.

BRIEF DESCRIPTION OF THE DRAWINGS

The present invention will now be described with reference to the accompanying drawings in which.

DESCRIPTION OF THE PREFERRED EMBODIMENTS

Figure 1:
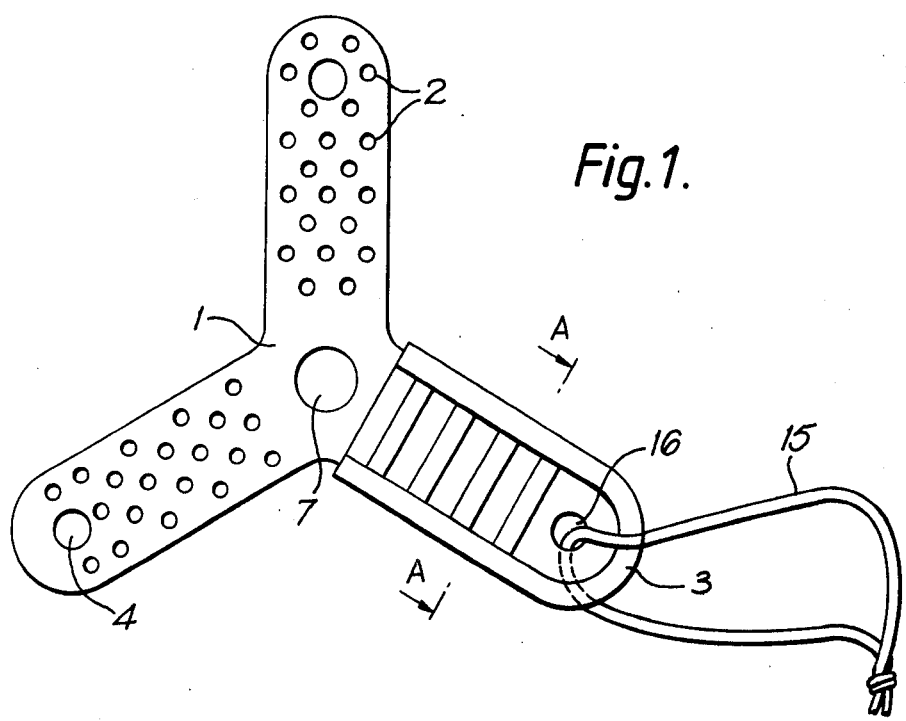
FIG. 1 is a spread out view of a device according to the invention having one lobe of the device coated with a skin, the other two lobes representing the skeleton.
Figure 2:
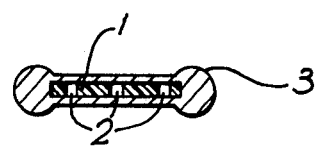
FIG. 2 is a cross section on the line AA FIG. 1.
Figure 3:
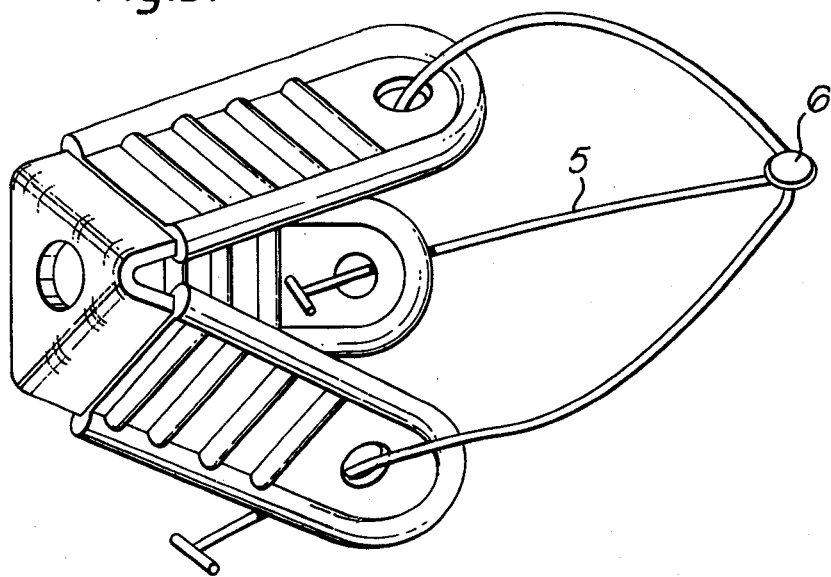
FIG. 3 is a particular sketch of the device including a withdrawal arrangement.
Figure 4:
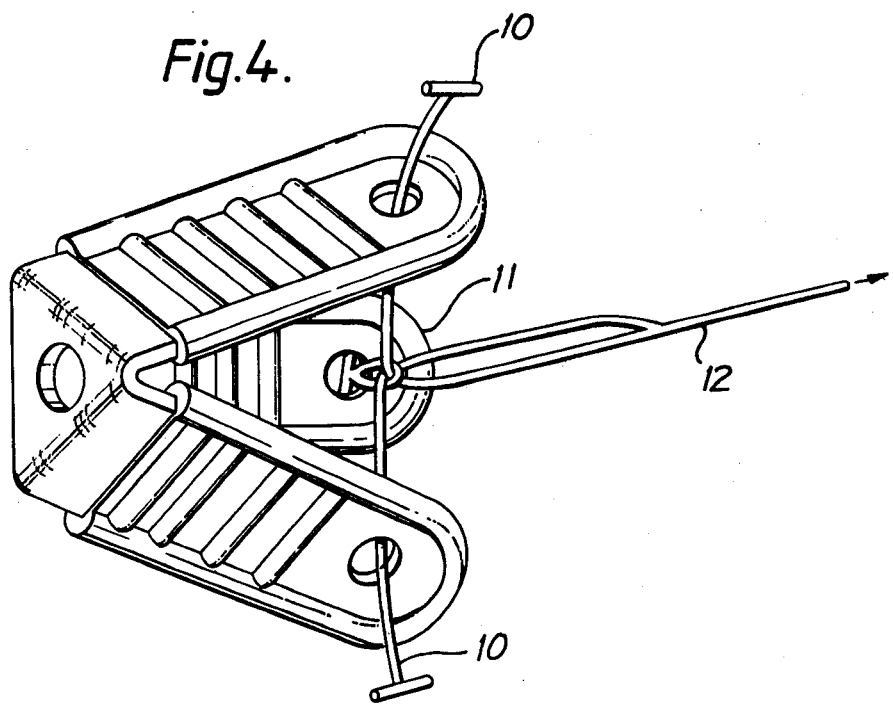
FIG. 4 is a perspective sketch showing a different type of withdrawal arrangement.

Referring to the drawings, in FIG. 1 a body 1 is moulded with a plurality of arms or lobes for example between 3 and 7 from a suitable plastics material such as polypropylene polyethylene or ethylene vinyl acetate which are non-toxic and flexible materials. Each of the lobes is perforated with a network of holes 2 as shown in FIG. 2 so that a drug carrying or active ingredient carrying polymer coating 3 may be moulded around at least the free ends of the lobes of the body 1 so that the active ingredient is provided in the skin and at least adjacent the surface thereof while the lobes form the skeleton of the device. Because the active ingredient is in the skin, it is available on the surface thereof for its pharmaceutical property. At the other end of each of the lobes of the body 1 is a hole through which may be threaded a withdrawing ligament 5 which may be moulded as a separate unit with a "T" shaped head on each length of the ligament the other end of each length being joined to a connecting point of loop 6 so that tension may be applied to the loop 6 to withdraw the device from the animal. Alternatively ligament 5 may be moulded in one piece with body 1 to substantially eliminate post moulding assembly costs. Another possible rearrangement of the withdrawing filament or ligament is shown in FIG. 4 where the members 10 carrying the T ends on two of the lobes pass through a ring 11 on the third lobe and are connected to a single filament 12.

We have however found as a result of an extensive programme of application and removal of the devices, that the simplest and most effective method of effecting removal is to have a filament 15 (FIG. 1) (which may be mono filament or multi-filament cord) looped through a hole 16 in one lobe of the device to provide withdrawal action by pulling on that one lobe only. When this one lobe is pulled, the other two lobes will fold over and trail behind as the device is withdrawn from the animal. This has been proven to give most reliable withdrawal with the least possible risk of discomfort or damage to the animal.

After moulding of the body or skeleton 1 in the suitable non-toxic and flexible material, the skeleton 1 is transferred to another mould in which the polymer substance 3 is moulded. Such a substance is, for example, a modern rapid curing two component silicone rubber which is moulded around each of the lobes 1. Such a rubber is available from the Dow Corning Corporation and has curing times which vary from one month at ambient temperature to five seconds at 200° C. By using an appropriate temperature e.g. one approaching 200° C., this silicone rubber can be cured very rapidly. During moulding of silicone rubber the two components of the silicone rubber are introduced into the moulding machine just prior to injection. The active ingredient whether it be a progesterone or oestrogen or other substance is premixed with one of the silicone rubber components or alternatively may be dosed automatically as the two silicone rubber components are fed into the mould of the moulding machine.

The foregoing describes an intra-vaginal device of particular configuration but other physical configurations are possible with the device which is characterised by being simply and cheaply produced by normal moulding such as injection moulding in two stages, firstly by moulding a skeleton or carrier and secondly by coating that carrier as required with a suitable substance e.g. a polymer which acts as a drug release polymer coating. We have found that a two part high speed curing silicone rubber is a feasible substance in this regard.

As may be seen from the drawings the surfaces of the skin are extended by indentations or undulations so that the surface area exposed to body fluids is increased. Such undulations or indentations may have a smooth profile so they do not unnecessarily collect or harbour bacteria or collections of bodily substances.

A central orifice 8 may be provided in the carrier moulding to allow for draining or flow of bodily fluids and/or withdrawal of the device by means of a suitably attached cord should this be preferred to the arrangements above described.

The insertion of the device may be effected by folding the lobes into a closed position after which the natural elasticity of the lobes will cause these to open against the internal surfaces of the vagina or other bodily orifice to retain the device in said position securely and without discomfort to the animal.

While the incorporation of drugs in a polymer device and its removal at the end of a treatment period does not completely eliminate the problems of residues, it is more acceptable to many approving authorities and they will consider a procedure such as induction of lactation, by the administration of oestrogens via a polymer device where injections of oestrogens are completely unacceptable.

In addition, sustained release of drugs has many other advantages. The amount of drug (or other substances) required to achieve a desired effect is often substantially reduced compared with injection or ingestion. Where substances are ingested the uptake by the gut and the metabolism of the entro-hepatic circulation offer substantial barriers to the effectiveness of materials reaching the target site.

Also, the passage of material through the gut is essentially a limiting factor to the effective time of an oral dose of a substance. With both injections and oral dosing, the material is usually in a soluble form and reaches high concentrations both at the site of administration and in the blood. This can cause complications both through local toxicity and in other parts of the body. As the clearance of a material is proportional to its concentration this means that usually, a large amount of injected material is wasted when sufficient is injected to act over a 24 hour period because of the high clearance at the time of such blood levels. With sustained release, the blood level of material can be maintained at much closer to the effective level. This frequently means that as well as reducing or avoiding toxicity problems, the amount of administered material is substantially reduced often by a factor of 100 or more.

The release of drugs from polymers has a wide variety of applications to animal production in New Zealand and in other countries. Many drug carrying devices have been devised and their descriptions published.

These have all suffered from limitations either in their effectiveness in use, damage or discomfort to the animal and/or the cost effectiveness and/or high labour cost of production.

Devices have been described for assistance in synchronisation of oestrus in sheep and cattle, for induced lactation in cattle, for induced calving etc.

Testosterone treatment of cows induces them to perform male mounting behaviour, so assisting in the detection of animals which are ready for mating.

It is possible to stimulate lactation by the administration of growth hormones; and many other possibilities exist for the application to animals of various minerals and drugs for a number of reasons.

For example one or more mineral trace elements in addition to or instead of a hormonal or oestrogenic or anthelmintic ingredients may be incorporated in the skin during manufacture thereof. In such cases the skin may be of ethylene vinyl acetate or other polymer and may be integral with the body or skeleton of the device.

The body or skeleton acts as a mechanical framework or support and the skin is an outer covering of sufficient thickness so that in use the skin erodes away freeing the active ingredient over a satisfactory period of time, the active ingredient being leached out by action of the animal's body fluids.

What is claimed is:

1. An intravaginal device for the sustained release of a physiologically active substance into the vagina of a mammal when inserted therein, including a resilient physiologically-inactive supporting skeleton and a polymeric coating having a physiologically-active ingredient incorporated therein moulded over said skeleton to form a physiologically-active skin thereupon, said physiologically active ingredient and said skin affording a sustained release of said physiologically-active ingredient during contact with the body fluids of said mammal, and said skeleton including means for increasing the surface area of the physiologically-active skin exposed to said body fluids comprising at least three broad lobes radiating in a plane from a central body portion, each of which lobes is perforated with a network of holes over which the skin is moulded to provide an undulated skin surface over said skeleton and increase the skin surface area exposed to body fluids.

2. An intra-vaginal device as claimed in claim 1 wherein said sleleton includes at least three intercontrolled lobes foldable to lie close to each other for insertion or removal.

3. An intra-vaginal device as claimed in claim 2, wherein said lobes are intercontrolled by a withdrawing ligament associated with the free end of each of the lobes.

4. An intra-vaginal device as claimed in claim 1 wherein said device is formed as a two part member by first forming the skeleton and then forming said skin on said skeleton, said skin having said active ingredient incorporated therein during moulding of the skin onto the skeleton.

5. An intra-vaginal device as claimed in claim 1 wherein said skin is formed integrally with the skeleton.

6. An intra-vaginal device as claimed in claim 5 wherein said skin is formed from ethylene vinyl acetate.

7. An intra-vaginal device as claimed in claim 1 wherein said skeleton is moulded of a suitable non-toxic and flexible material comprising polypropylene or polyethylene.

8. An intra-vaginal device as claimed in claim 1 wherein said skin is formed from a high-speed curing silicone rubber.

9. An intra-vaginal device as claimed in claim 8 wherein said high speed curing silicone rubber is a two component silicone rubber.

10. An intra-vaginal device as claimed in claim 9 wherein said active ingredient is premixed with one of the silicone rubber components before mixing of the two components in a moulding machine just prior to injection.

11. An intra-vaginal device as claimed in claim 9 wherein said active ingredient is dosed automatically as the silicone rubber components are fed into moulding parts of a moulding machine.

12. An intra-vaginal device as claimed in claim 1, wherein said active ingredient is selected from one or more of progesterone, oestrogen, testosterone; or mineral trace elements comprising selenium cobalt copper, and boron; or anthelmintics.

13. An intra-vaginal device as claimed in claim 1 having at least three lobes, and further including means for withdrawing the device from the vagina comprising a filament attached to the free end of one of the lobes so that the remaining lobes flex and fold over within the vagina and trail behind as the filament is pulled and the device withdrawn.

14. An intra-vaginal device as claimed in claim 1, wherein the mammal is a sheep or cow.

15. The intravaginal device of claim 1, wherein the skin is moulded over the skeleton by injecting a two-component liquid silicone rubber containing a physiologically-active ingredient over the skeleton in a mould, and curing the rubber at an elevated temperature.

* * * * *